(12) United States Patent
Woodard et al.

(10) Patent No.: US 6,893,436 B2
(45) Date of Patent: May 17, 2005

(54) ABLATION INSTRUMENT HAVING A FLEXIBLE DISTAL PORTION

(75) Inventors: Robert E. Woodard, Hayward, CA (US); Hiep Nguyen, Milpitas, CA (US); Dany Berube, Milipitas, CA (US)

(73) Assignee: AFX, Inc., Santa Clara, CA (US)

( * ) Notice: Subject to any disclaimer, the term of this patent is extended or adjusted under 35 U.S.C. 154(b) by 16 days.

(21) Appl. No.: 10/039,872

(22) Filed: Jan. 3, 2002

(65) Prior Publication Data

US 2003/0125720 A1 Jul. 3, 2003

(51) Int. Cl.[7] .............................................. A61B 18/18
(52) U.S. Cl. ....................................... 606/41; 607/101
(58) Field of Search .......................... 601/2; 604/95.01, 604/95.04, 525, 528; 606/41, 45, 47, 32; 607/98, 101

(56) References Cited

U.S. PATENT DOCUMENTS

| | | | |
|---|---|---|---|
| 5,800,482 A | * | 9/1998 | Pomeranz et al. .......... 607/101 |
| 5,823,955 A | | 10/1998 | Kuck et al. |
| 6,102,886 A | * | 8/2000 | Lundquist et al. ............ 604/22 |
| 6,245,062 B1 | | 6/2001 | Berube et al. |
| 6,277,113 B1 | | 8/2001 | Berube |

FOREIGN PATENT DOCUMENTS

| | | |
|---|---|---|
| EP | 0839547 | 5/1998 |
| WO | WO 02/38052 | 5/2002 |

OTHER PUBLICATIONS

Gauthier et al, " A Microwave Ablation Instrument With Flexible Antenna Assembly And Method" U.S. patent application No. 09/484,548 filed Jan. 18, 2000.

Dany Berube, " Electrode Arrangement for Use in A Medical Instrument," U.S. patent application No. 09/548,331, filed Apr. 12, 2000.

Mody et al " A Tissue Ablation and Apparatus with a Sliding Ablation Instrument and Method," U.S. patent application No. 09/751,472, filed Dec. 28, 2000.

* cited by examiner

*Primary Examiner*—Michael Peffley
*Assistant Examiner*—Aaron Roane
(74) *Attorney, Agent, or Firm*—Fenwick & West LLP

(57) ABSTRACT

An ablation instrument having a flexible portion at or near the distal portion of the instrument, is provided. The instrument includes an elongated tubular member having a steerable distal end configured to deflect, or otherwise direct, and properly position at least a portion of the distal portion, comprising an ablation device, during an ablation procedure. The instrument further includes a deflectable member which cooperates with the steering system allowing for the proper placement of the ablation device adjacent or proximate to the target tissue surface. The steering system may alternatively be incorporated into a separate guiding catheter as part of the catheter system.

5 Claims, 17 Drawing Sheets

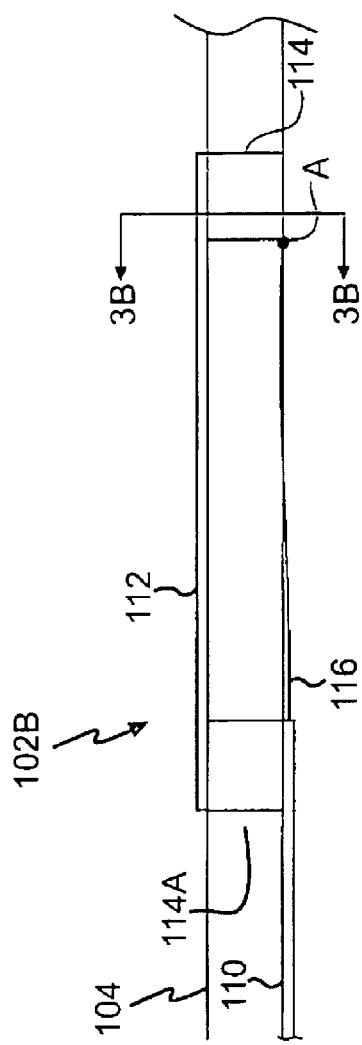
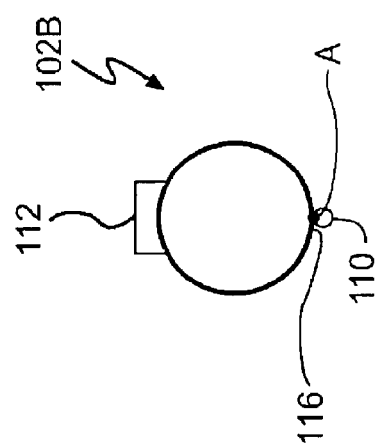

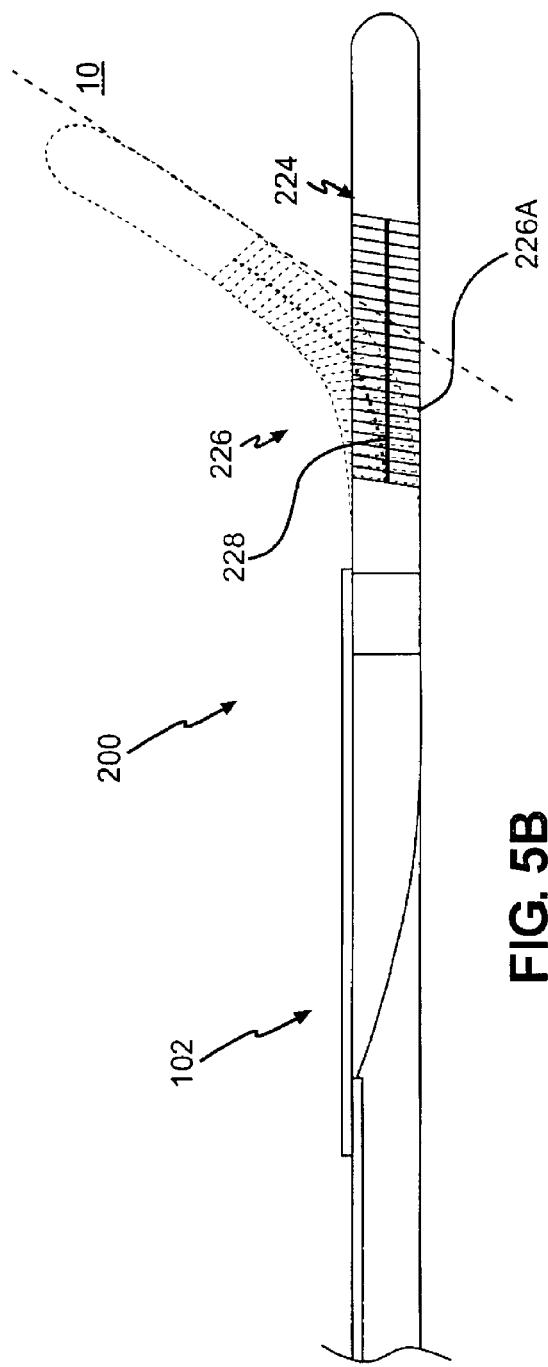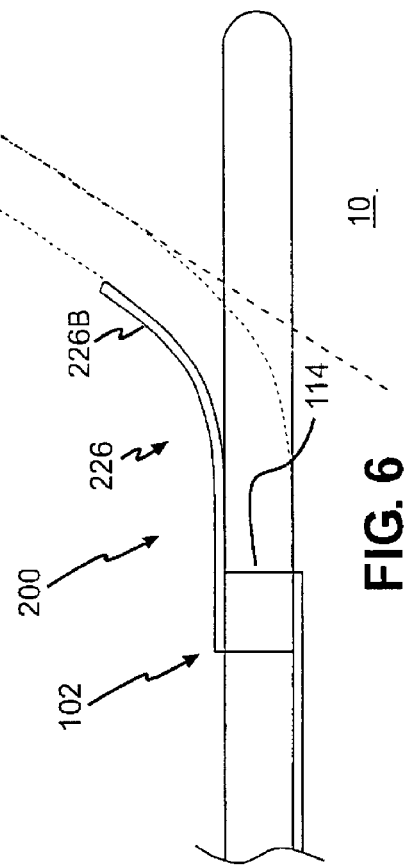

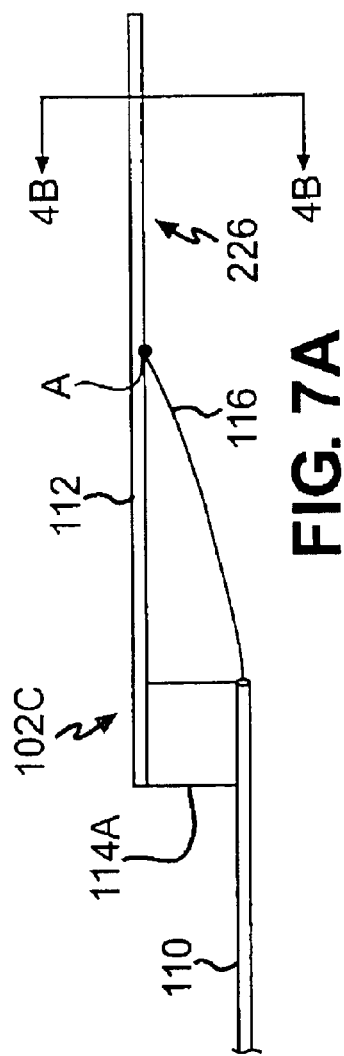
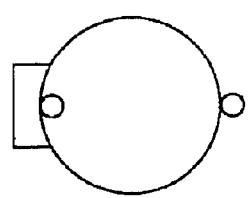
FIG. 7A
FIG. 7B

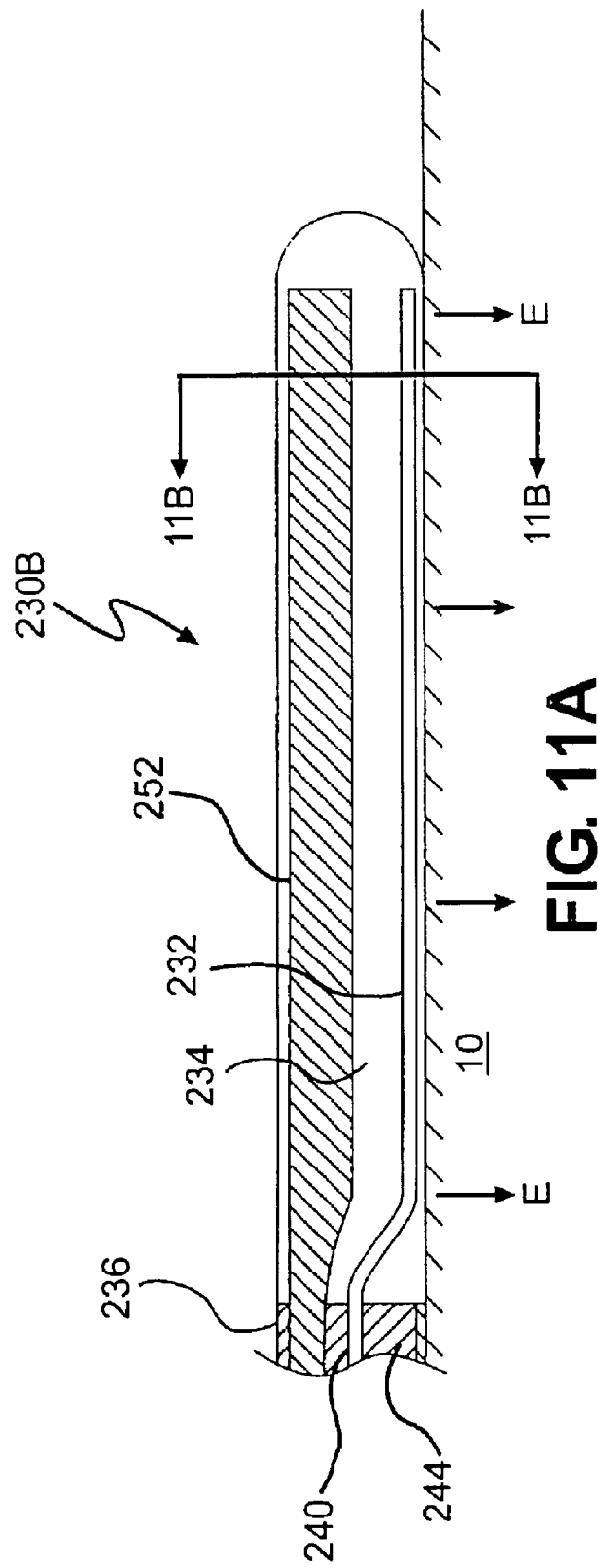

ABLATION INSTRUMENT HAVING A FLEXIBLE DISTAL PORTION

BACKGROUND OF THE INVENTION

1. Field of Invention

The present invention relates generally to catheter systems used in diagnosis and treatment of various body tissues and, more specifically, to steering systems incorporated into catheter systems for ablating cardiac tissue in the treatment of electrophysiological diseases.

2. Description of the Related Art

As is well know, catheters provide medical professionals access to various interior regions of the human body, in a minimally invasive manner, in support of diagnosis and treatment. Catheters allow such professionals to place one or more medical instruments, pharmacological agents or other matter at a target tissue site. For example, in cardiac procedures in support of diagnosis and treatment of atrial fibrillation, catheters provide access to various chambers of the heart, carrying ablation devices which translate therein to such sites for ablation of specific cardiac tissue associated with atrial fibrillation.

Ablation of tissue, cardiac tissue for example, is directly related to the orientation of the ablation element from which energy sufficient to ablate biological tissue is emitted. For such procedures, precise control of the ablation device is desirable to ensure proper placement of the ablation element utilized in creation of one or more desired lesions. As a surgeon, or other medical professional, manipulates the proximal end of the catheter system, the distal end of the catheter must be responsive to such movement in a very predetermined, smooth-flowing and proportional way.

Proper placement of an ablation device is exasperated by the fact that some ablative energy technologies require energy transmission conduits which are bulky, or otherwise constructed from materials less flexible, making the distal portion of the catheter difficult to properly position. For example, distal portions of optical fiber or microwave based ablation systems, or catheter systems comprising an endoscopic device, may be more difficult to maneuver due to the lack of {flexibility in the transmission mediums utilized therein. As should be readily apparent, when the distal portion of an ablation catheter system is not properly positioned, ablative energy is not properly directed and applied to the target tissue, resulting in poor lesion formation. It is therefore essential that the ablative device be able to be manipulated and sufficiently controlled to be properly positioned to transfer the requisite energy to ablate biological tissue and create a desired lesion therein.

SUMMARY OF THE INVENTION

Accordingly, it is a general object of the present invention to provide a catheter system which resolves the above-identified problems. Another object of the present invention is to provide a catheter system which ensures proper placement of an ablation device upon a target tissue to be ablated. Another object of the present invention is to provide a catheter system which incorporates a steering system having an enhanced mechanical advantage for deflecting inflexible systems contained therein.

Yet another object of the present invention is to provide a catheter system incorporating a steering system adapted to smoothly deflect ablation systems contained therein. Still another object of the present invention is to provide a catheter system which ensures proper placement of an ablation device proximate a target tissue site during creation of an intermediate lesion as part of a long continuous lesion.

These and other objects are achieved through systems disclosed herein. More specifically, a system for ablating a selected portion of biological tissue at a target tissue site is provided. The system is particularly suitable to ablate cardiac tissue within the right atrium and includes a tubular member having a distal end including an ablative device which, in turn, includes one or more ablation elements adapted to emit ablative energy therefrom, and a steering system operably attached to a proximal section.

Still another object of the present invention is to provide a catheter system incorporating an enhanced steering or deflection system adapted to transmit steering or deflecting forces from a distal portion of the catheter system to a proximal portion thereof.

It is a further object of the present invention to provide a catheter system which allows for the delicate control of the positioning of an ablation device thereof upon the isthmus between the inferior vena cava and the tricuspid valve.

In one embodiment, the ablation device may also include a shielding means adapted to be opaque with respect to the corresponding ablative energy utilized, protecting tissues surrounding a target tissue site from the ablative energy. Additionally, the shielding means may be configured to reflect at least a portion of the ablative energy toward the target tissue site to facilitate or encourage tissue ablation and lesion formation.

In another embodiment, the system further includes a flexible intermediate section. The flexible intermediate section includes a springy member configured to allow the distal portion, including the ablation device, to deflect and return to its normal position relative to a proximal section of the catheter system. In another embodiment, the flexible intermediate section comprises a coil spring which provides additional support to the tubular structure, as well as the deflecting functionality. The coil spring may also include means to promote deflection of the flexible intermediate section in at least one geometric plane.

In still another embodiment, the ablation device is a microwave antenna assembly which includes an antenna configured to emit microwave ablative energy. The ablation device may also include a shielding means coupled to the antenna assembly. The shielding means may be adapted to substantially shield a surrounding area of the antenna from the electromagnetic field radially generated therefrom while permitting a majority of the field to be directed generally in a predetermined direction toward the target tissue site. Alternatively, the shielding means, in another embodiment, may be adapted to absorb the electromagnetic energy transmitted therefrom protecting surrounding tissues. The ablation device may further include an insulator which functions to hold the shielding means and antenna in fixed relationship with respect to each other and a target tissue site, further controlling the ablative characteristics of the ablation device.

In yet another embodiment, the steering system is part of an elongated guiding member having at least one lumen passing therethrough, the tubular member of the catheter translating therein.

In another embodiment, the steering system includes a tubular member having at least one lumen passing therethrough and adapted to transmit steering or deflecting forces from a distal portion of the catheter to a proximal portion of the tubular member. The proximal end of the tubular member may be elongated and fixedly attached to a handle portion.

While the ablative energy is preferably electromagnetic energy in the microwave range, other suitable energies include, but are not limited to, cryogenic, ultrasonic, laser, chemical and radiofrequency.

In another aspect of the present invention, a method for treatment of a heart includes directing the ablation device into a patient's vasculature; guiding the distal end of the ablation device into a chamber of the patient's heart; manipulating the ablation device until the distal portion is proximate to a target tissue site; and applying ablative energy to the tissue.

In another aspect of the present invention, the method for treatment of a heart further includes a step of manipulating the distal portion such as to ensure proper position of the ablative device proximate and parallel to the target tissue such that a long continuous lesion is created.

In one embodiment, the step of manipulating is performed by incrementally sliding, or otherwise moving, the ablative device along a predefined ablation path to produce a long and substantially continuous lesion.

Other objects and attainments together with a fuller understanding of the invention will become apparent and appreciated by referring to the following description and claims taken in conjunction with the accompanying drawings.

BRIEF DESCRIPTION OF THE DRAWINGS

FIG. 3A is a side view of another embodiment of a steering system in accordance with the present invention.

FIG. 3B is an end view of the steering system of FIG. 3A.

FIG. 5B is a side view of a catheter system incorporating an alternative embodiment of the flexible intermediate section of FIG. 5A.

FIG. 6 is a side view of a catheter system incorporating another embodiment of a flexible intermediate section in accordance with the present invention.

FIG. 7A is a side view of another embodiment of a steering system in accordance with the present invention.

FIG. 7B is an end view of the steering system of FIG. 7A.

FIG. 11A is a detailed side view of another embodiment of an ablation device used in accordance with the present invention.

DETAILED DESCRIPTION OF THE INVENTION

While the present invention will be described with reference to a few specific embodiments, the description is illustrative of the invention and is not to be construed as limiting the invention. Various modifications to the present invention can be made to the preferred embodiments by those skilled in the art without departing from the true spirit and scope of the invention as defined by the appended claims.

Figure 1A:
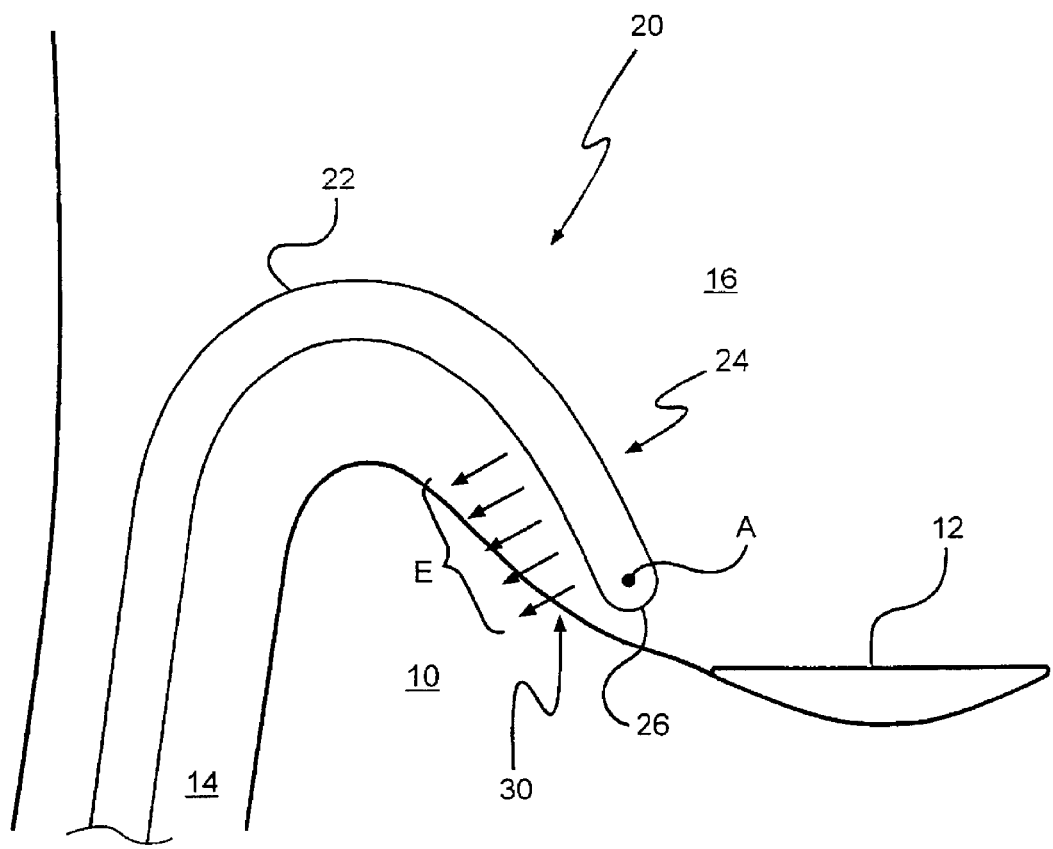
FIG. 1A is a side view of a catheter system having a steering system know in the art.

Turning to FIG. 1A, a catheter 20 is shown within a chamber of the heart. More specifically, FIG. 1A depicts catheter 20 advanced from a point proximate to the femoral vein (not shown), through the inferior vena cava 14 (IVC), and into the right atrium 16, a distal tip 26 of catheter 20 engaging cardiac tissue 10, between the IVC 14 and tricuspid valve 12. For purposes of clarity, the depiction of the cardiac structure has been simplified.

The catheter 20 comprises a long tubular member 22 having a proximal portion (not shown) and distal portion 24, the proximal portion operably attached to a handle portion (not shown). The distal portion 24 includes, or otherwise incorporates, an ablation device 30 including one or more ablation elements. The one or more ablation elements are arranged and configured to emit ablative energy in a lateral direction generally away from an emission surface of the catheter 20 body, as shown, a portion of the radiating energy designated by the arrows E and the emission surface corresponding to the outer catheter surface from which the energy is emitted, with respect to catheter 20. For purposes of the discussion herein, radiating energy shall generally refer to energy transfer of any kind corresponding to the specific configuration of the ablation device. In this light, arrows E more specifically represent the desired energy pattern emitted from distal portion 24. For example, given an ablation device comprising a plurality of RF electrodes on the outer surface of distal portion 24, arrows E represent the desire to have the lateral surface area of the electrodes, as part of distal portion 24, contact target tissue which leads to creation of thermal energy sufficient for tissue ablation.

The steering system of catheter 20 typically comprises at least one pull wire operably attached to a deflecting means as part of the handle portion (not shown) and the distal portion 24 at attachment point A. Operation of the deflecting means results in the deflection of distal portion 24 of catheter 20. Since the attachment point A is close to the distal end 26 of distal portion 24 it is often difficult for an operator, an electrophysiologist for example, to manipulate the distal portion 24 in such a way as to position the emitting surface substantially proximal and parallel to heart tissue 10 in order to create a desired lesion therein. As depicted in FIG. 1A, with an improperly positioned distal portion, a substantial portion of the ablative energy fails to effectively engage tissue 10. Rather, the energy is absorbed in the blood. The operator may attempt to properly position distal portion 24 by slightly retracting catheter 20. Typically, with reference to FIG. 1A, the apex of tissue 10 formed at the opening of the IVC interacts with body 22 of catheter 20 preventing proper placement of distal portion 24, irregardless of the force used.

Figure 1B:
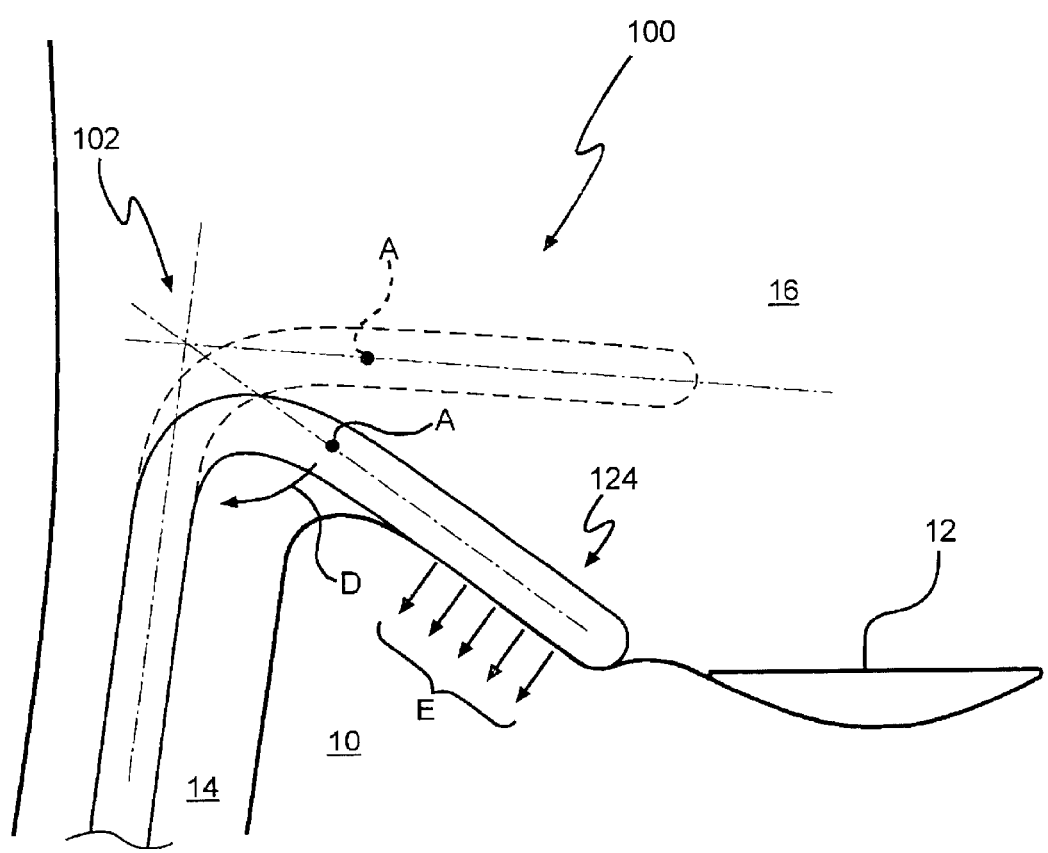
FIG. 1B is a side view of a catheter system including a steering system in accordance with the present invention.

Now turning also to FIG. 1B, a catheter 100 is shown incorporating a steering system in accordance with the present invention. Catheter 100 incorporates a steering system 102 having a distal attachment point A located proximal to distal portion 124. Therefore, as should be readily apparent from FIG. 1B, as the catheter 100 is deflected from an initial position (shown in dashed line), point A moving in a direction indicated by arrow D, the portion of catheter 100 distally located from point A remains unaffected by the deflection, maintaining its natural, substantially straight, orientation. Such a configuration allows the distal portion 124 of catheter 100 to be placed proximal and substantially parallel to target tissue 10, allowing the emitted energy E to fully, and more effectively, impact upon target tissue 10, ensuring proper lesion formation.

Furthermore, steering system 102, as is discussed in greater detail below, is further configured to reduce the mechanical force needed to steer or deflect the catheter, allowing for the deflection of generally inflexible catheter structures, for example endoscopes and the like. Additionally, the reduced force required to deflect the catheter allows the User to apply additional contact force between the ablation device and the tissue. This increased contact force flattens or otherwise encourages the target tissue to contact the ablation device in such a way as to promote proper tissue ablation and lesion formation. Therefore, for illustration purposes only, since the isthmus between the IVC and the tricuspid valve is somewhat concave as depicted throughout the figures of the present application, the application of the additional contact force would allow the distal portion of the catheter to flatten or encourage the isthmus to contact the catheter along the length of the distal portion.

Alternatively, steering system 102 may be incorporated into a separate guiding catheter (not shown), such that the ablation device of an ablation catheter translates therein. It should also be noted that while the ablative device may be described as being parallel to a target tissue, this does not necessary mean the orientation of the ablative device is straight or linear. For example, the ablative device may be curved to address the natural curvature of an internal organ, the ablative device directed to the target tissue through the use of a guiding catheter configured to hold the ablative device in a linear orientation until the ablative device emerges and takes on its predetermined form.

Catheter 100 may take on numerous configurations while maintaining the spirit of the present invention. In general, catheter 100 comprises an inner catheter structure 104 and an outer catheter structure 106, with which the steering systems disclosed herein are designed to cooperate. The inner and outer catheter structures 104, 106 may comprise components typically found in catheter systems known in the art. For example, the inner structure 104 may be integral to catheter system 100 carrying medical devices, sensors or other instruments to a target tissue point within a body, such that structure 104 is fixedly attached to one or more components of the catheter 100 steering system. Alternatively, structure 104 may be configured to translate within a lumen of outer structure 106, whereby the catheter 100 steering system 102 may be fixedly attached to structure 106.

Now referring to FIGS. 2–5, steering systems in accordance with the present invention shall be discussed in greater detail. In general, steering system 102 is operationally disposed between a deflecting means within a handle portion (not shown) and distal portion 124 of catheter 100. Except for the embodiment of FIG. 5 discussed in more detail below, steering system 102 comprises an elongated tubular member 110, a deflectable member 112, at least one attachment member 114, and a pull wire 116.

Tubular member 110 comprises at least one lumen passing therethrough adapted to accept and allow the pull wire 116 to translate therein. Pull wire 116 is operably disposed between the deflecting means within the handle portion (not shown) and a component of steering system 102, advantageously arranged to maximize the mechanical advantage therein. Activation of the deflecting means results in translation of wire 116 and a corresponding deflection of steering system 102. The deflection means may comprise one or more of the following, along or in combination: slide switches or push button switches either mechanically or electrically controlled, springs, pulleys, sliders, levers, or any other device which assists in the effective translation of wire 116.

The specific configuration of tubular member 110 depends on the flexibility of catheter system 100. For a less flexible catheter system 100, member 110 preferable runs the length of catheter 100 and fixedly attaches to the handle portion. In this way, pull wire 116 is concentrically confined within member 110 over the length of catheter 100, directing deflection forces associated with the operation of steering system 102, and transmitted by member 110, to the handle portion, limiting undesirable flexing of catheter 100 along its length which may result in unwanted tissue damage. Additionally, with the tubular member 110 running the length of catheter 100, member 110 protects inner catheter structure 104 from translation movement of wire 116.

Alternatively, the tubular member 110 may be short, the inner catheter structure 104 then providing the requisite stability to prevent tissue damage as described immediately above. In this case, tubular member 110 may be fixedly attached to catheter structures 104, 106 using any suitable means, such as by epoxy bonding, shrink molding, or the like. Additionally, tubular member 110 can be fixedly attached to outer catheter structure 106 allowing for translation of catheter structure 102 with respect to the steering system 102 described herein. Attachment member 114 may be fixedly attached to, or allowed to float with respect to, inner catheter structure 104 depending upon the specific configuration of catheter 100, as discussed in more detail below.

Tubular member 110 may be a hypotube of any suitable material, such as various metals and plastics. Alternatively, tubular member 110 may be a tightly wound spring, of a suitable material, adapted for greater flexibility of the catheter 100 while still providing the requisite rigidity needed to transmit mechanical forces and enable proper deflection of member 112.

Figure 2A:
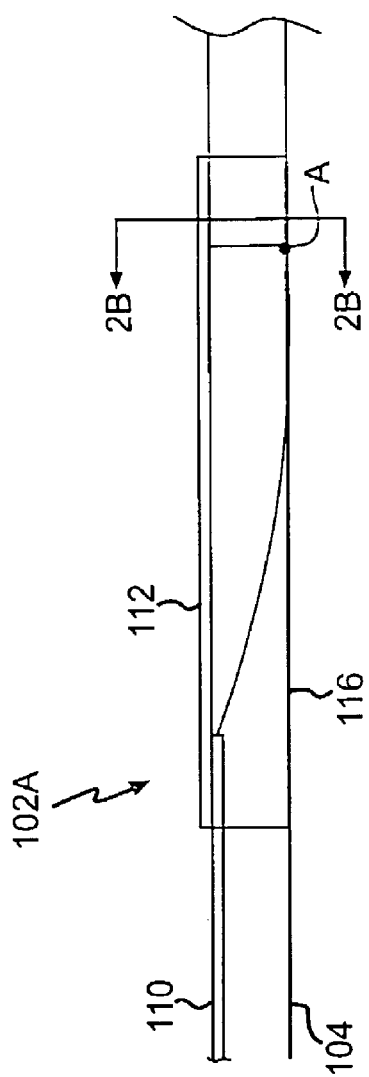
FIG. 2A is a side view of a first embodiment of a steering system in accordance with the present invention.

As shown in FIG. 2A, deflectable member 112 of steering system 102A operably attaches to a distal end of tubular member 110. Deflectable member 112 is springy in nature allowing for the deflection of an intermediate portion 108 of catheter 100, such that, as the pull wire 116 translates in a first direction the steering system 102 deflects a portion of catheter 100 and as wire 116 translates in a second direction, the deflected portion of catheter 100 resumes its undeflected orientation, substantially straight as depicted.

Deflectable member 112 may be made from any suitable material having the ability to be deflected upon application of an external force and then returning to its initial orientation when the external force is removed, such as springy stainless steel, nitinol, or the like. While the member 112 is shown having a rectangular cross-section, other geometric cross-sections are also contemplated in accordance with the present invention. The geometry of the cross-section defines, or otherwise further limits, the flexibility characteristics of member 112. In one embodiment, member 112 has a rectangular cross-sectional area, having a width greater than a height, such that, deflectable bending of member 112 is restricted to substantially one geometric plane. It should be noted that various other cross-sectional geometries of member 112 will lead to more specific catheter configurations when steered or otherwise deflected. Additionally, the cross-sectional geometries of member 112 may change along its longitudinal axis further defining the resulting orientation of distal portion 124 when deflected.

The distal end of member 112 is operably attached to attachment member 114, either to its external surface (as shown) or its internal surface. Member 114 also provides an attachment point A for wire 116. As shown with reference also made to FIG. 2B, attachment point A is at a point on member 114 furthest away from deflectable member 112. In this way, a mechanical lever arm of maximum length is defined allowing the steering system 102 to deflect less flexible catheter systems, as further described above.

While the attachment member 114 is shown configured as a thin-walled ring member, constructed from a 1 mm section of 15TW hypotube for example, member 114 can be configured in any suitable geometric shape pertinent to the configuration of the catheter 100 itself. For example, the catheter 100 may be constructed in such a way as to make a ring impractical. Other geometric shapes may, therefore, be utilized having cross-sectional geometries including, but not limited to, transverse rectangular, semi-circular, beam, or any other geometries holding attachment point A a sufficient distance from the distal end of member 112, establishing a mechanical lever arm. FIGS. 2C and 2D depict geometric cross-sectional shapes of member 114. FIG. 2C depicts member 114 as a beam member whose height dimension is greater than its width dimension such that the beam member can withstand applied bending forces required during operation of steering system 102. FIG. 2D depicts member 114 as a semicircular member allowing for a nonsymmetrical catheter cross-section.

It should be apparent that member 114 can also take on other geometric cross sectional shapes and stay within the spirit of the invention. Additionally, member 114 may comprise more than one geometric form. For example, member 114 may be formed from numerous substantially tubular bodies, such that the cross-sectional geometry is honeycomb in nature. In such a system each tubular body may be designed to cooperate with a component of inner structure 104, a separate elongated tubular member having at least one lumen passing therethrough for example, holding each separate elongated member in fixed relationship with the others. The elongated members may be used, for illustration purposes only, for the transport of fluids such as saline, liquid or semi-liquid drugs, ablative energy elements such as cryogenic or chemical material, or components of the ablation device itself, such as one or more optical fibers or one or more cryogenic tubules.

Alternatively, it should be noted that one or more components of steering system 102 may be incorporated into catheter structures 104, 106. Additionally, structures 104, 106 may be constructed from materials which provide the functionality of one or more components of steering system 102, such as the deflectable member 112 or attachment member 114, or both. For example, inner catheter structure 104 may comprise a lumen of which a portion, proximate to the distal opening of tubular member 110, is constructed from suitable materials having resilient properties similar to member 112. In this case, pull wire 116 would exit the distal opening of member 110 at a first radial position about catheter structure 104 and be fixedly attached a predetermined length from the distal end of member 110 to the structure 104 at a second radial position, preferably 180° from the first radial position, through epoxy bonding or the like.

Figure 2B:
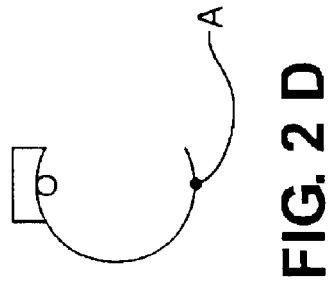
FIG. 2B is an end view of the steering system of FIG. 2A.
Figure 2C:
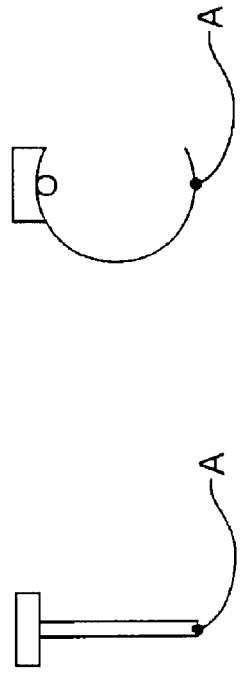
FIGS. 2C-D illustrate geometric cross-sectional shapes of members of the steering system in accordance with embodiments of the present invention.
Figure 2D:
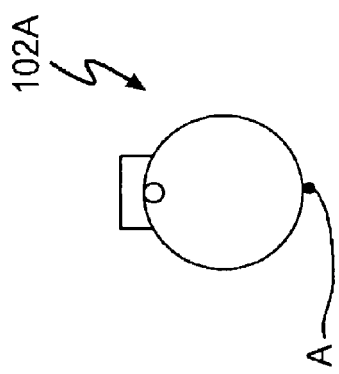

As shown in FIGS. 2A and 2B, wire 116 exits a distal opening in tubular member 110 and attaches to attachment member 114 at point A. This attachment may be achieved using any know means compatible with the material composition of wire 116 and member 114, including, but not limited to, epoxy bonding, laser brazing, or the like. Pull wire 116 of steering system 102A may pass in a semi-circular manner about a longitudinal length of inner catheter structure 104. (The pull wire 116 is not shown in the sectional views for clarity purposes). It is important to note, however, that the semi-circular path depicted is particular to that particular catheter system and the actual path taken by pull wire 116 for any given catheter system is a function of the inner catheter structure therein. For example, the path of pull wire 116 from the distal opening of tubular member 110 to attachment point A may be generally linear if the inner structure 104 was configured to permit such a path.

For catheter systems configured for multiple use, e.g. may be sterilized for reuse, such a configuration may be undesirable since wire 116 may chafe or otherwise wear on inner catheter structure 104. With reference made to FIGS. 3A and 3B, an alternative steering system 102B is shown which overcomes undesirable wear, as described immediately above.

As shown in FIGS. 3A and 3B, steering system 102B, as compared to system 102A, further comprises attachment member 114A operably disposed between tubular member 110 and deflectable member 112. In this system, pull wire 116 is held substantially parallel to inner catheter structure 104, minimizing abrasive wear between wire 116 and structure 104 during deflection. In this embodiment, attachment member 114 may float with respect to catheter structure 104 while either 114A or tubular member 110 remains fixedly attached to inner structure 104, as previously discussed with reference to member 114 and member 110 of steering system 102A above.

As with the embodiment of FIG. 2A, since member 114A is rigidly attached to both, member 110 and member 112, member 114 acts as a lever arm with respect to wire 116 attachment point A and the distal end of member 112. As stated above, it is this mechanical advantage which allows for the deflection of catheter systems which, due to their construction, are less flexible. The ablative energy utilized will dictate the required energy transmission medium as part of catheter system 100 and, therefore, the overall flexibility of the catheter system.

Figure 4:
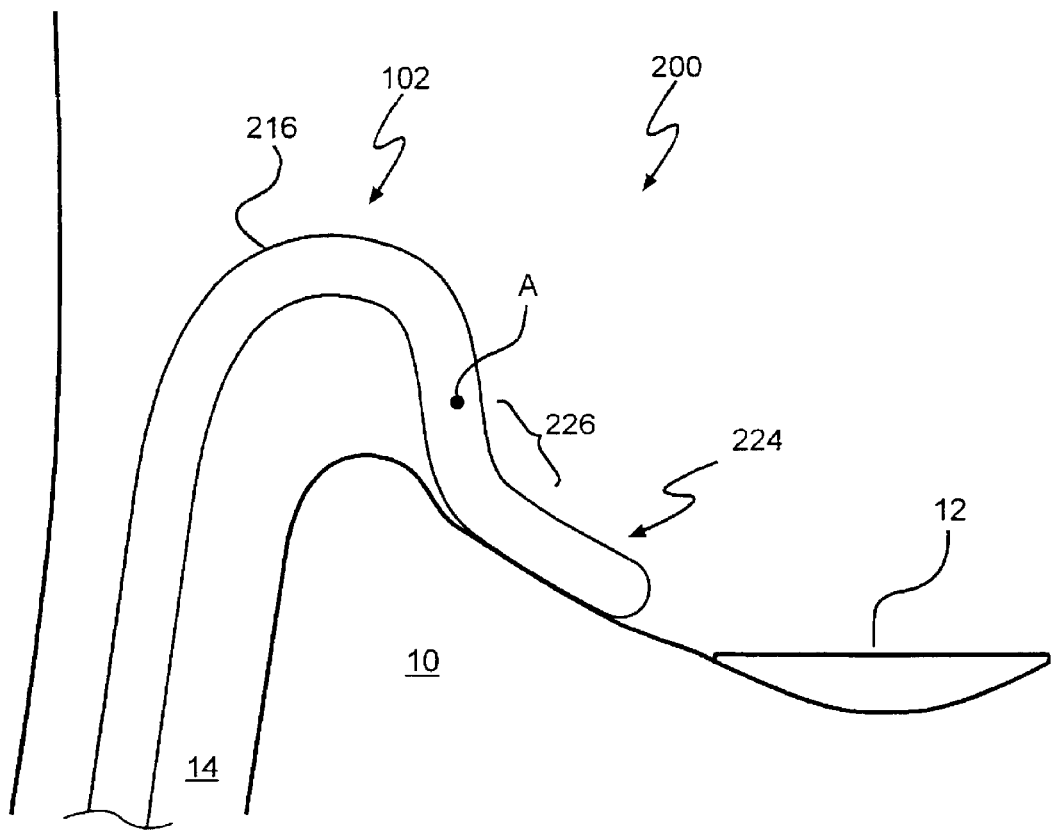
FIG. 4 is a side view of a catheter system incorporating a flexible intermediate section in accordance with the present invention.

With reference now to FIG. 4, another catheter system 200 is shown incorporating steering system 102 in accordance with the present invention. More specifically, catheter system 200 comprises an elongated tubular member 222, a steering system 102, an inner catheter structure 204, an outer catheter structure 206, and a flexible means 226 located proximal to distal portion 224. The flexible means 226 of catheter 200 allows for further dynamic deflection of distal portion 224 with respect to a point immediately proximal to portion 226. Additionally, As will become readily apparent, flexible portion 226, cooperating with steering system 102, allows for the incremental ablation along a desired lesion path, the isthmus between the IVC and tricuspid valve being one example of such a desired lesion path.

Figure 5A:
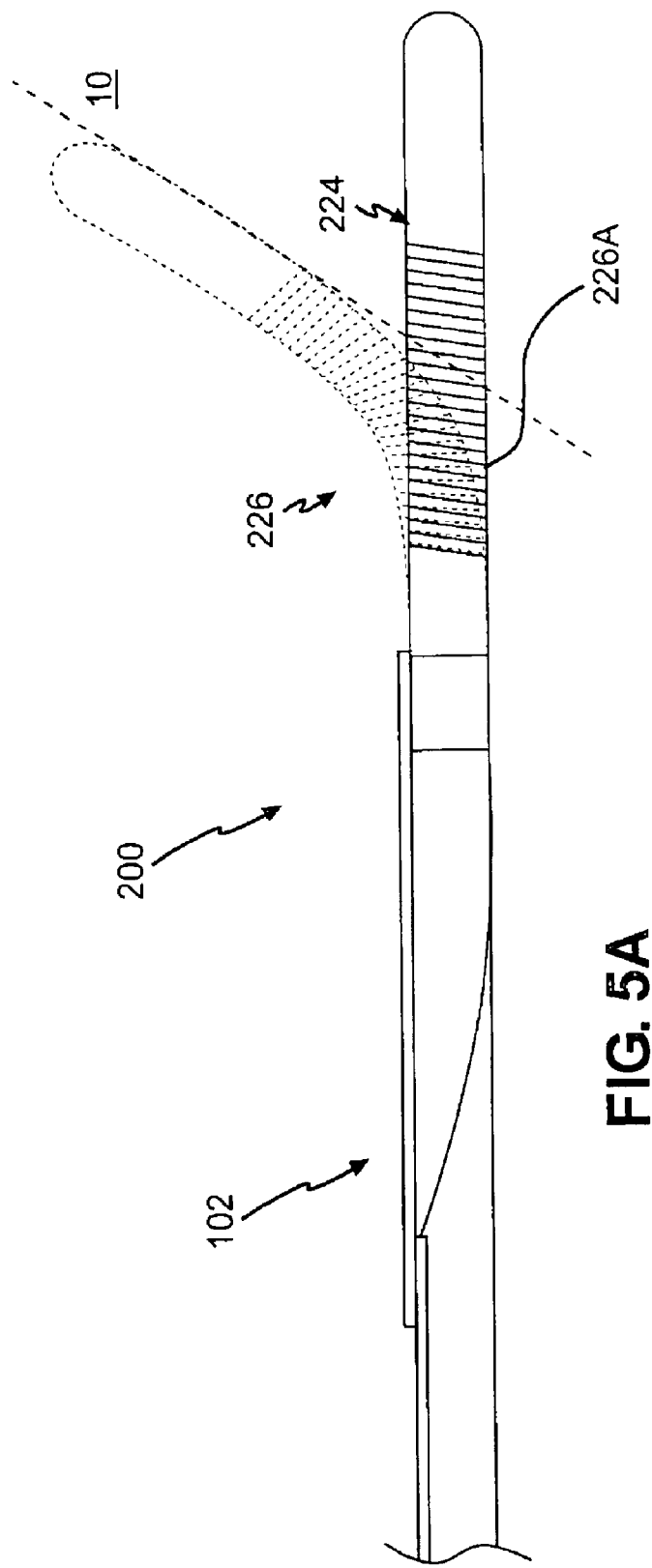
FIG. 5A is a side view of a catheter system incorporating a first embodiment of a flexible intermediate section in accordance with the present invention.

Now turning also to FIGS. 5A, 6 and 9, catheter 200 incorporating flexible means 226 will be discussed in more detail. FIG. 5A depicts a first embodiment of a catheter system 200 incorporating a flexible means 226. As shown, catheter 200 comprises steering system 102 located proximal to flexible means 226. While FIG. 5A depicts steering system 102A, any steering system 102 discussed, or otherwise contemplated herein, may be utilized as required by the specific configuration of catheter 200.

Flexible means 226 comprises a coil spring element 226A which, upon application of an external force upon distal portion 224 by target tissue 10 allows distal portion 224 to deflect to a position as shown in dashed-line. As will become readily apparent, as catheter system 200 is further manipulated, movement of the ablation device upon target tissue 10 along a desired path is achieved through operation of means 226.

With reference now made to FIG. 5B, another embodiment of catheter system 200 is shown wherein flexible portion 226A further comprises one or more support members 228. Support members 228 longitudinally placed along the outer circumference of flexible portion 226A restricting the flexibility of portion 226A to one geometric plane, preferably in a plane perpendicular to support members 228.

Alternatively, with reference to FIG. 6, a second embodiment of a catheter system 200 incorporating a flexible portion 226B is shown. Flexible portion 226B allows for the same functionality as portion 226A, discussed immediately above. More specifically, flexible portion 226B is constructed from any suitable biocompatible material allowing for the desired deflection of distal portion 224 upon contact and application of an external force thereon, as discussed above. Alternatively, flexible portion 226B may be an extension of member 112, as part of steering system 102A, beyond ring member 114. Generally, flexible portion 226B extends from about 0.5 cm. to about 2.0 cm. beyond ring member 114, however this depends directly on the specific configuration of the ablation device utilized.

With reference now to FIGS. 7A and 7B, another embodiment of steering system 102 will be discussed. Steering system 102C is similar to steering system 102B, however lacks distal ring member 114 and further includes a distal flexible means 226. The distal end of pull wire 116 is attached at a predetermined attachment point A along the length of member 112. The attachment point A is defined by the ablation system utilized and the desired flexibility required such that the distal portion of the ablation device can engage the specific target tissue of interest during use. For example, for microwave based systems which utilize a linear ablation element and RF based systems which utilize one or more electrodes mounted along the distal length of the ablation device, the attachment point would be more proximally located along member 112 to allow the distal portion of the ablation device to engage the target tissue over substantially its entire length.

As with steering systems previously discussed, as pull wire 116 translates in tension, deflection member 112 deflects, the distal end of member 112 acting to also deflect inner catheter structure 104. When wire 116 translates in an opposite direction, the tension force is removed and member 112 resumes its natural undeflected state, returning inner catheter structure 104 to a corresponding substantially straight undeflected position, as stated above with respect to other embodiments.

As with steering system 102A, with specific reference to FIG. 7B, the pull wire 116 travels about the inner catheter structure 104. As the catheter structure is deflected there can be wear to inner structure 104, as discussed above. Therefore, while steering system 102C may be utilized in any deflectable catheter system 100, steering system 102C is preferably utilized for single use catheter systems 100.

Figure 8A:
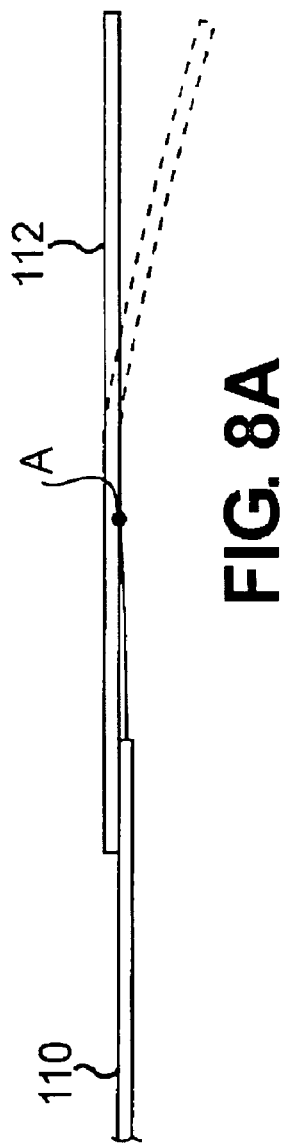
FIG. 8A is a side view of another embodiment of a steering system in accordance with the present invention.
Figure 8B:
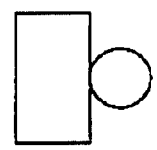
FIG. 8B is an end view of the steering system of FIG. 8A.

Now turning to FIGS. 8A and 8B, an alternative embodiment of steering system 102 is shown for use with catheter systems 100 more flexible in nature. As shown, steering system 102D comprises tubular member 110 and deflectable member 112. The distal portion of tubular member 110 is fixedly attached to the proximal portion of member 112. The pull wire 116 is attached at a predetermined attachment point A along the length of member 112. As stated above, the exact attachment point A is determined for the particular material used in the construction of member 112 such that member 112 deflects without substantial undesirable bending or deflection. For illustration purposes only, a suitable deflection orientation is shown in dashed line.

While steering system 102D does not utilize the mechanical advantage element of steering systems 102A–C, system 102D allows for the deflection of the distal portion 124 of the catheter system 100 allowing the distal portion 124 to be placed substantially proximal and parallel to a target tissue site, such as the isthmus between the IVC and the tricuspid valve as discussed above. Additionally, with the simple construction of system 102D, such a system can be made smaller, allowing for entry into smaller areas of a body.

Figure 9A:
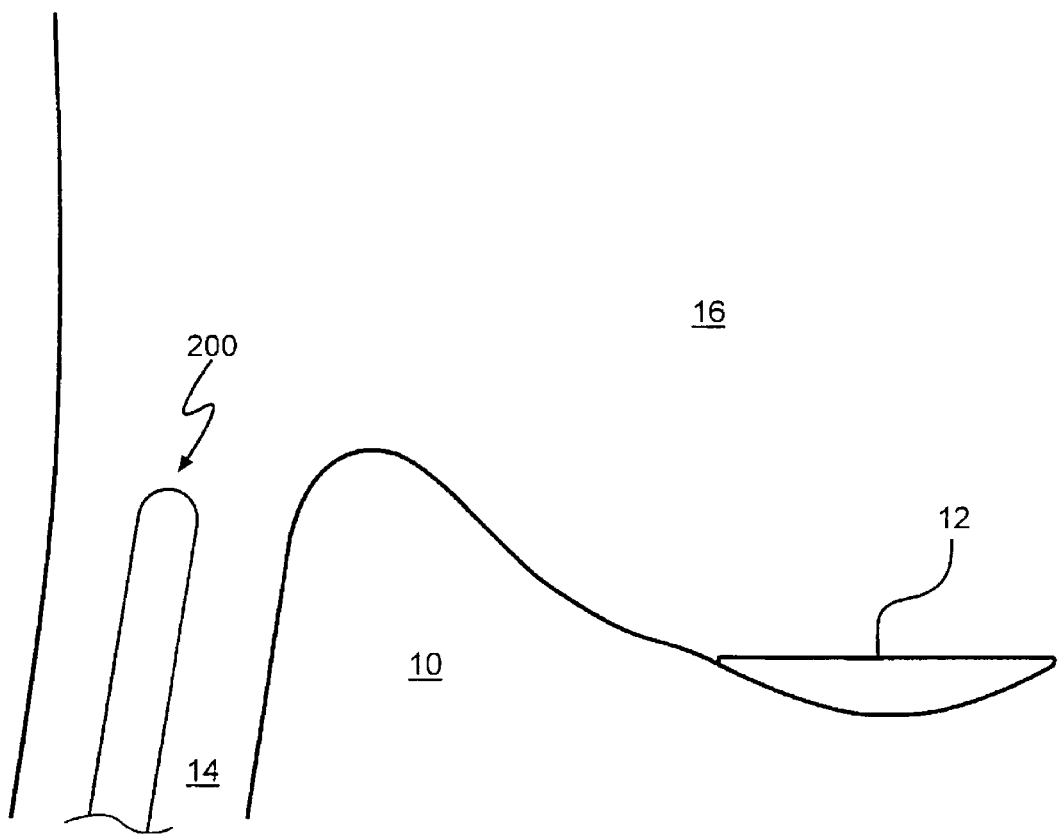
FIGS. 9A–D are side views of a catheter system being deployed in accordance with the present invention.
Figure 9B:
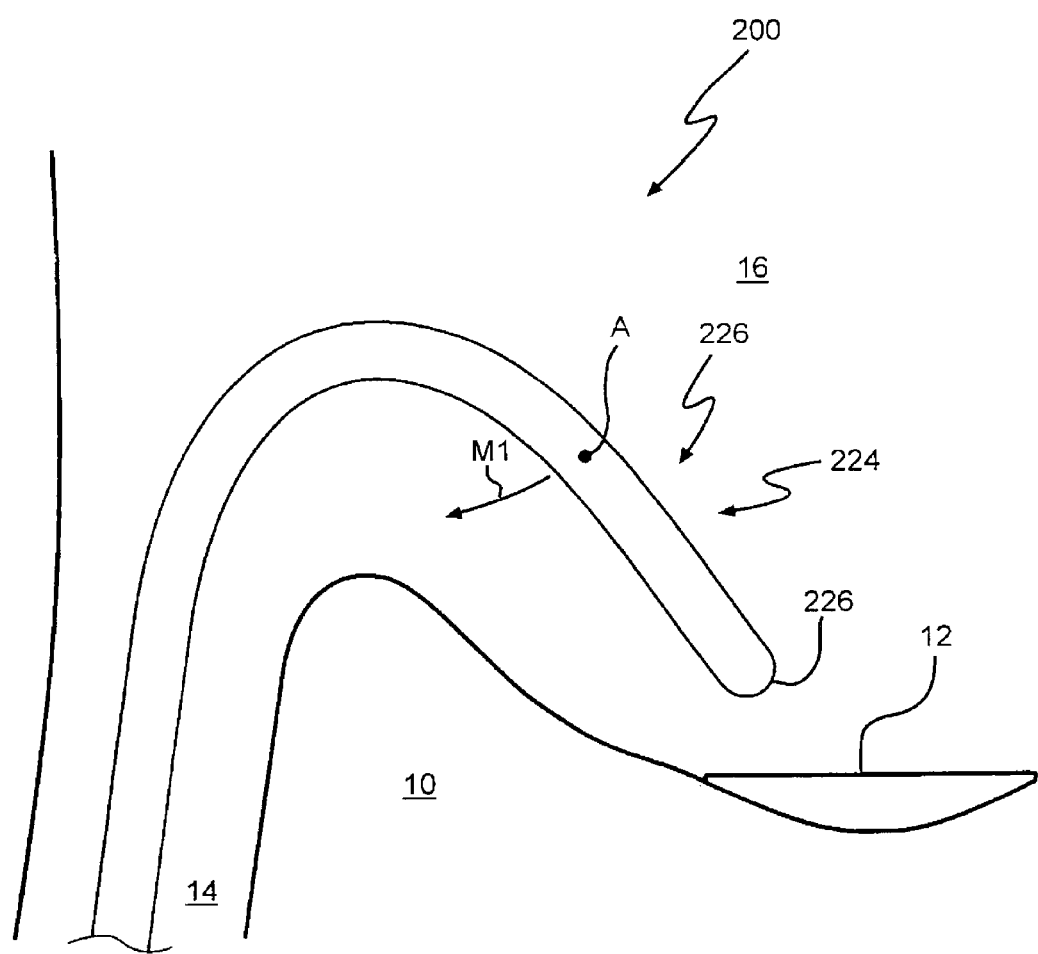
Figure 9C:
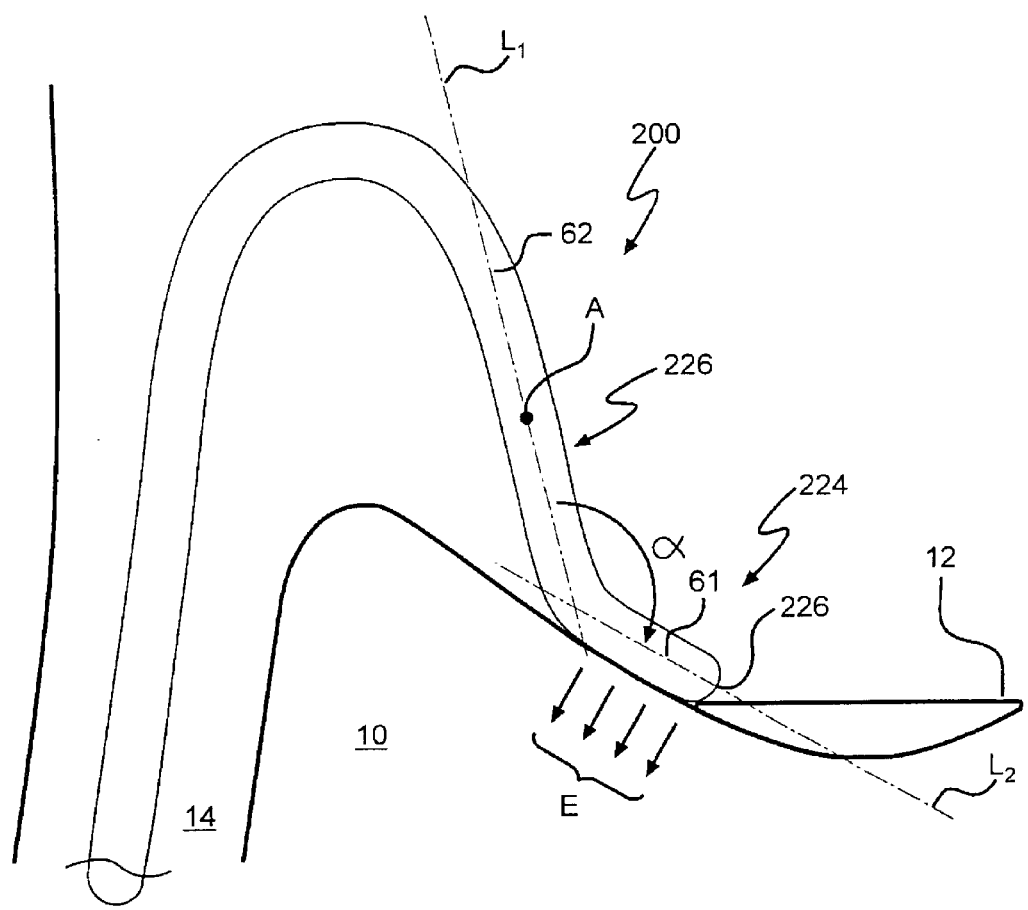

Now turning to FIGS. 9A–9C, the operation of catheter system 200 can be more readily understood. While FIGS. 9A–9C depict the ablation, or otherwise medical treatment, of the isthmus between the IVC 14 and tricuspid valve 12, it should be apparent that such a system 200 can be utilized in other areas of the body or in association with other bodily organs, hollow or otherwise. As shown in FIG. 9A, catheter 200 is depicted advancing intravascularly from a point proximal to the IVC 14, the femoral vein for example, toward the target tissue site.

Now referring specifically to FIG. 9B, as the distal portion 224 of catheter 200 enters the right atrium 16, the steering system 102 acts to deflect distal portion 224 to direct distal tip 226 in a direction generally toward the tricuspid valve 12. As is depicted, and as should be readily understood, once the distal portion 224 is within the right atrium, the catheter 200 is no longer advanced, however, distal portion 224 is continually deflected by operation of the controlling means within the handle portion, controlling the deflection of steering system 102, as described in greater detail above. Continued operation of the steering system 102 results in further deflection of distal portion 224, attachment point A moving generally in a direction noted by arrow M1.

As is readily understood with reference made specifically to FIGS. 9B and 9C, as the distal tip 226 of portion 224 engages target tissue 10, flexible portion 226 deflects allowing the distal portion 224 to be placed substantially proximal and parallel to the surface of target tissue 10. Deflection of portion 224 made possible by flexible portion 226 allows for proper application of ablative energy E to tissue 10 for tissue ablation resulting in the desired lesion formation.

Figure 9D:
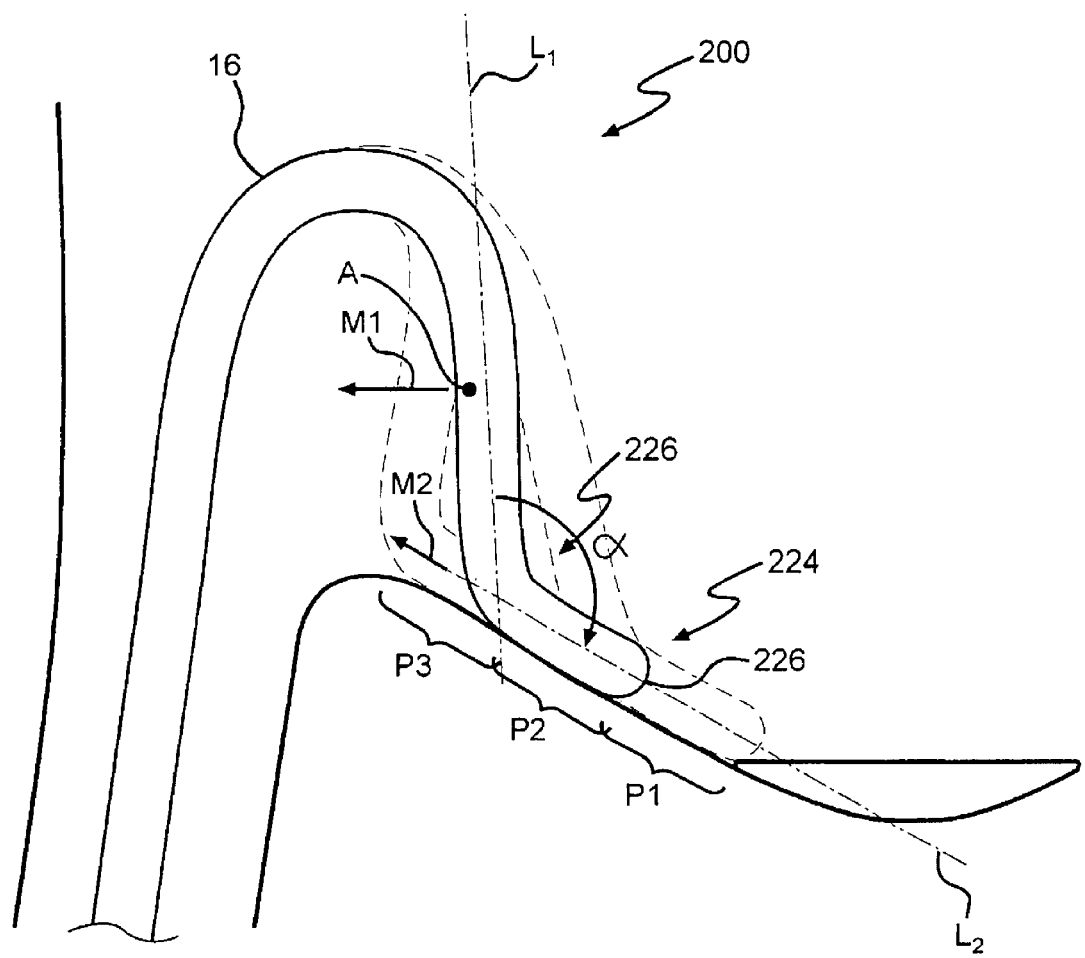

When the flexible portion 226 deflects, an angle α is defined between a longitudinal axis of distal portion 224 and a longitudinal axis of a point immediately proximal to flexible portion 226, as depicted by centerlines L1 and L2, respectively, in FIG. 9C. With reference also to FIG. 9D, it should be apparent that, as the steering system 102 further deflects an intermediate portion of catheter 200 and attachment point A moves in a general direction indicated by arrow M1, the elbow defined by the flexible portion moves in a general direction indicated by arrow M2. It should be apparent that arrows M1 and M2 define a general direction of movement and as the intermediate section 218 is further deflected the movement of corresponding locations actually include vector components in additional directions.

It should also be apparent that the advancement of distal portion 224 across the isthmus can be further controlled by incorporating an expandable element, a mesh basket for example, into outer catheter structure 206 (not shown). The expanding element can expand within the IVC 14, engaging the walls thereof, holding the catheter 200 body within the IVC 14 stationary while allowing blood to flow therethrough. Optionally, to better position the catheter 200 body such that the distal portion can better engage a portion of the target tissue 10, two such expandable elements can be utilized. Each expandable element is placed along the outer catheter structure 206 a predetermined distance from each other, further defining the orientation of the catheter as it enters the atrium.

Now with specific reference to FIG. 9D, a process of ablating a target tissue will be discussed. As described above, distal portion 224 is placed substantially proximal and parallel to target tissue 10. Upon initial placement, with the tip 226 of distal portion 224 directly adjacent to tricuspid valve 12, ablative energy sufficient to ablate tissue 10 to a sufficient depth to treat atrial flutter is applied creating an initial intermediate lesion at position P1.

After the initial lesion corresponding to P1 is created, catheter 200 is further deflected such that distal portion 224 is advanced along tissue 10 toward the IVC 14 opening until an overlapping position, depicted as P2, is reached. Once again, ablative energy is emitted from distal portion 224 and a second intermediate lesion corresponding to position P2 is created. Once again the catheter is deflected, as described above, until distal portion 224 is positioned at overlapping position P3. Ablative energy is once again emitted and a corresponding intermediate lesion is formed in tissue 10 at position P3. The intermediate lesions at positions P1–P3 collectively resulting in a desired long continuous lesion along the isthmus.

While the above procedure is described in terms of three lesions, the actual number of overlapping lesions is a function of the ablative energy utilized and the configuration of distal portion 224 comprising ablative device 230. For example, the length of the intermediate lesion created is a direct function of the dimensional characteristics of the ablation device utilized. Therefore, the desired resultant long continuous lesion may comprise the creation of fewer or greater intermediate lesions than described above.

Ablative device 230 may also include an energy shielding means adapted to be impermeable to the ablative energy utilized, such that, tissue adjacent to target tissue 10, for example, is protected from the ablative energy. Furthermore, is should be noted that the energy shielding means can be further adapted to reflect the ablative energy in a predetermined and desirable fashion as to focus the ablative energy at a desired region of the target tissue 10, whereby the lesion characteristics can be better controlled.

For example, the shielding means may be formed to reflect and direct microwave energy in a relatively thin line along the longitudinal axis of the antenna, resulting in the desired formation of a relatively thin long intermediate lesion. Alternatively, the shielding means of a cryo based system may be constructed from thermal isolating material, the shielding means axially surrounding a substantial portion of ablative device 230 leaving only a relatively thin opening along the longitudinal axis of device 230, corresponding to a desired lesion. The opening would be controllably directed toward target tissue 10, as discussed above, to create an intermediate lesion. As discussed above, flexible member 112 of steering system 102 may be constructed as to limit the deflection of intermediate portion 218 to one plane, ensuring, for example, that the opening of the cryo-based ablation device 230, discussed immediately above, is directed toward target tissue 10. Other methods of directing ablative energy may include, but are not limited to, RF insulation, laser focusing, ultrasound focusing, or any other method utilized in specific placement of ablative energy at a desired point 1n space.

While the ablative device 230 is preferably adapted to emit microwave energy sufficient to ablate the target tissue upon which a lesion is desired, other ablative energies utilized by an ablative device 230 in catheter 200 may include, but is not limited to, one or more of the following energies, along or in combination: microwave energy, laser energy or other forms of light energy in both the visible and non-visible range, radio frequency (RF) energy, ultrasonic energy, cryogenic energy, chemical energy, resistive heating, or any other energy which can be controllably emitted and directed at least towards a portion of a desired target tissue, transporting thermal energy to the target tissue at sufficient energy levels resulting in tissue ablation and corresponding lesion formation.

One exemplary ablation device 230 comprises a monopole microwave antenna as disclosed and further described in commonly owned U.S. Pat. No. 6,277,113, entitled "Monopole Tip for Ablation Catheter and Methods for Using Same," which is hereby incorporated herein by reference, in its entirety. Alternatively, ablation device 230 may comprise other microwave antenna structures as disclosed and further described in commonly owned U.S. Pat. No. 6,245,062, entitled "Directional Reflector Shield Assembly for a Microwave Ablation Instrument," U.S. patent application Ser. No. 09/484,548, filed Jan. 18, 2000, entitled "Microwave Ablation Instrument With Flexible Antenna Assembly and Method", and U.S. patent application Ser. No. 09/751,472, filed Dec. 28, 2000, entitled "A Tissue Ablation Apparatus with a Sliding Ablation Instrument and Method," all hereby incorporated herein by reference, each in its entirety.

Additionally, catheter 200 may further comprise one or more electrodes strategically placed upon the distal portion 224 to facilitate capture of certain electrophysiological signals. Such signals allow a User to determine tissue characteristics of a target tissue site and also provide confirmation that the distal portion 224 is properly positioned substantially proximal and parallel to a target tissue, for example. Such electrode arrangement systems may be similar to those disclosed in U.S. patent application Ser. No. 09/548,331, filed Apr. 12, 2000, entitled "Electrode Arrangement for Use in A Medical Instrument," hereby incorporated herein by reference, in its entirety.

With reference to FIGS. 10 and 11, two exemplary ablation devices as part of catheter system 200 are shown. The ablative energy utilized in the catheter system 200 of the embodiment of FIGS. 10 and 11 is preferably microwave energy in the range of from about 400 MHz to about 6 GHz.

With specific reference to FIG. 10, a first exemplary ablation device 230A is shown. Ablation device 230A comprises an ablation element 232 in the form of a linear antenna encased in an insulating material 234. Antenna 232 is adapted to radiate electromagnetic energy radially about its structure over substantially its entire length, a portion of the radiated energy generally depicted by arrows E. Insulating material 234 acts to hold ablation element 232 a fixed distance from the target tissue, tissue 10 for example, when the ablation device 230A is placed proximal to, or engaging, the tissue, as depicted. For the ablation device 230 depicted, the insulator is a low-loss dielectric material able to transmit a substantial portion of ablative energy therethrough. Such materials may include, but are not limited to, TEFLON®, silicone, polyethylene, polyimide, or other materials having similar properties.

Figure 10A:
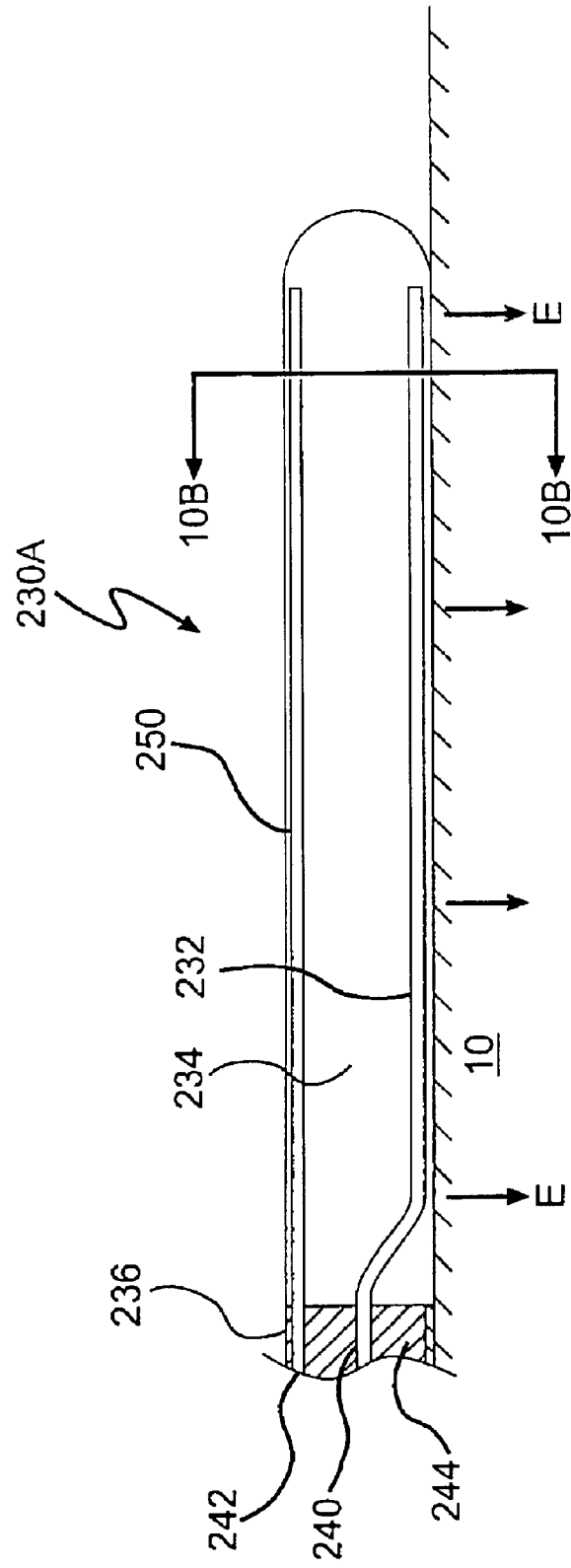
FIG. 10A is a detailed side view of an ablation device used in accordance with the present invention.

Ablation element 232 is electrically coupled to a transmission medium adapted for transmission of ablative energy from an energy source, a microwave generator for example, to ablation element 232. As depicted in FIG. 10A, transmission medium 236 comprises center conductor 240, an outer conductor 242, and an insulating material 244 therebetween. For example, transmission medium 236 may be a coaxial cable adapted to transmit energy to ablation element 232 at predetermined power levels sufficient for ablating the target tissue. Center conductor 240 is conductively coupled, or otherwise electrically connected, to a proximal end of ablation element 232.

The microwave generator may be any suitable generator able to delivery ablative energy to the ablation element at frequencies ranging from about 400 MHz to about 6 GHz, as stated above, and more preferably at one or more of the frequencies of about 434 MHz, 915 MHz, 2.45 GHz, and 5.8 GHz.

The antenna 232 can be formed from any suitable material including, but not limited to, spring steel, beryllium copper, or silver-plated copper. The diameter of antenna 232 may be from about 0.005 to about 0.030 inches, and more preferably from about 0.013 to about 0.020 inches.

It should be noted that the efficiency of ablation device 230A is directly related to the ability of transmission medium 236 to effectively transmit energy from the energy source to ablation element 232. Therefore, ablation device 230A may further comprise elements which maximize the efficiency of the ablation system. For example, these elements may comprise one or more electrical components which interface to one or more elements of the ablation system, comprising the energy source, transmission medium and ablation device, acting to match the impedance characteristics of, or otherwise tune, the ablation system itself. 24

Ablation device 230A may also include an optional stiffening member 250, as shown, to further ensure that ablation device 230A maintains its desired position proximal to a target tissue site during tissue ablation. As should be readily apparent, the length of stiffening member 250 will be limited by the openings through which catheter system 200 must navigate.

Figure 10B:
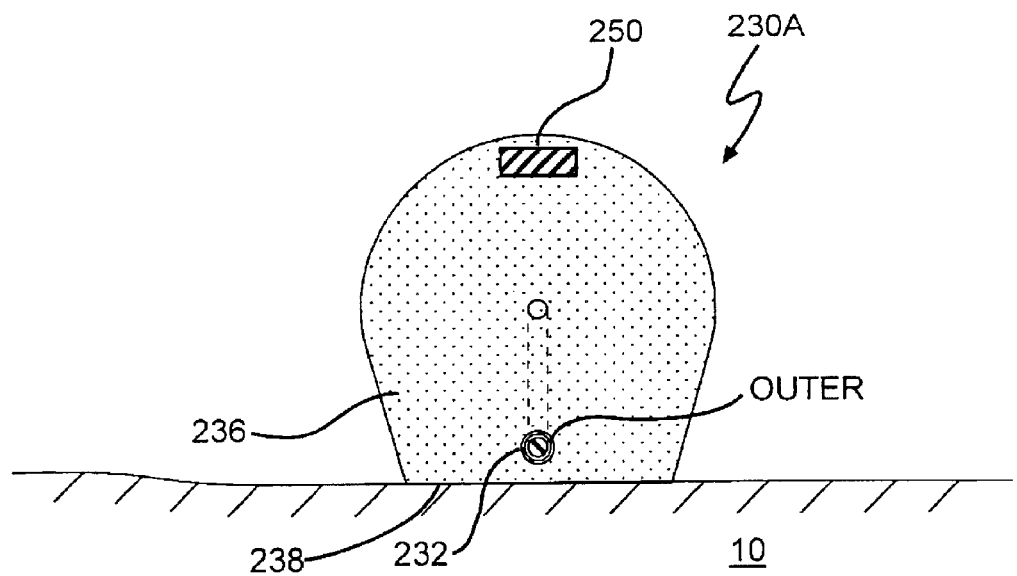
FIG. 10B is a detailed end view of the ablation device of FIG. 10A.

As is more readily understood with reference specifically to FIG. 10B, while ablation device 230 may take any suitable shape, ablation device 230A is shown to include a longitudinally flat surface 238 which aides in properly orienting ablation device 230A upon target tissue 10. Additionally, it should be noted that a catheter system 200 incorporating an ablation device 230 as depicted in FIGS. 10A and 10B may include a steering system 102 having a deflecting member 112 with a cross-sectional geometry limiting deflection of the distal portion 224 to one plane, as discussed above, further aiding in the proper placement of ablation device 230A upon tissue 10. It should be appreciated, however, that other ablation devices 230 may include linear antenna structures of varying shapes which are disposed coaxially within insulating material 234 and, thus, are not sensitive to a specific orientation of the ablation device upon the target tissue. The overall shape of the ablation device may therefore be cylindrical in nature.

Figure 11B:
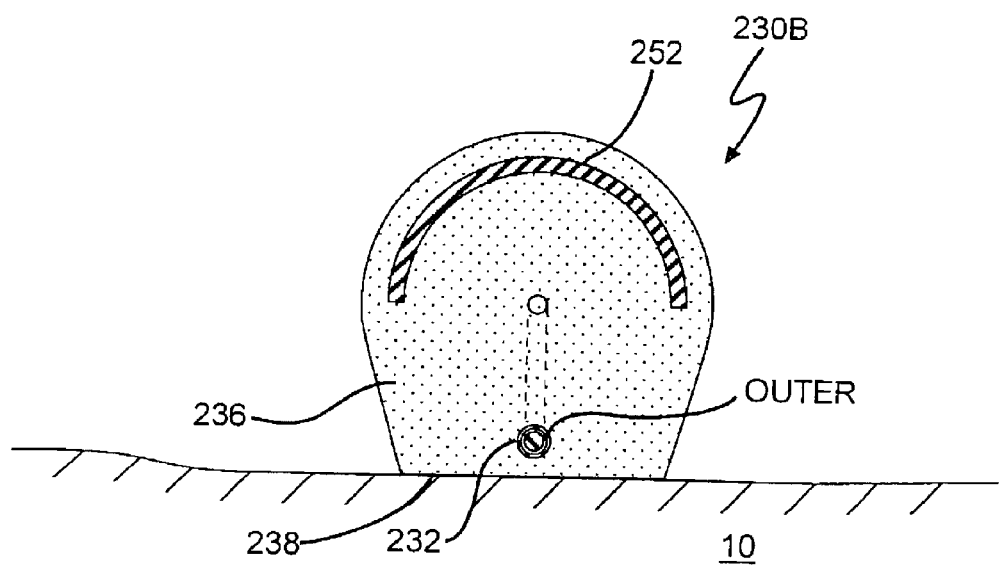
FIG. 11B is an end view of the ablation device of FIG. 11A.

Now with reference to FIGS. 11A and 11B, an alternative embodiment of an ablation device 230 is depicted. Ablation device 230B is similar to device 230A with the inclusion of a shielding means 252. As discussed in greater detail above, the shielding means 252 may act to absorb ablative energy, microwave energy in this case, reflect and redirect the ablative energy toward the target tissue to enhance ablation, or both. Reflection of the energy being a function of the construction material of shielding means 252 and redirection of the energy being a function of the geometric shape of shielding means 252. To facilitate absorption of the microwave energy, shielding means 252 may be formed from any suitable microwave absorption material, such as metal-impregnated silicone, polymers such as nylon, or water, or other suitable fluids, encased within distal portion 224. It should be noted that use of an absorption material may require additional cooling. Alternatively, the water, or other suitable fluid used to absorb the microwave energy may be configured to flow about the distal portion and remotely cooled.

To facilitate reflection of the ablative energy, shielding means 252 is preferably constructed from a highly conductive metal formed in a geometric shape having a semi-circular cross-section, as depicted specifically in FIG. 11B. The proximal end of the shielding means 252 is preferably electrically attached to outer conductor 242 of the transmission medium. As should be readily understood, the shielding means may be shaped to further reflect the energy in any desirable way. By way of example only, the shape of the shielding means may result in reflecting the energy in a focused manner, concentrating the energy in a longitudinally thin line along the length of ablation device 230B, as discussed above. Alternatively, shielding means 252 may be shaped to allow for a wider application of energy along the length of ablation device 230B. For such arrangements, the insulating means 234 provides the further function of decreasing the coupling between the antenna 232 and the shielding means 250, preventing undesirable substantial electrical current flowing therebetween.

Furthermore, shielding means 252 may be substantially planar in construction, formed from metallic foil for example. Alternatively, shielding means 252 may be constructed from a metallic wire mesh copper, the wire mesh having wire spacing sufficient to prohibit passage of the electromagnetic energy utilized therethrough.

It should be noted that the ablation device 230, like the device 230A, may optionally further comprise stiffening member 250. Alternatively, shielding means 252 may be constructed in such a manner as to provide the functionality of the stiffening member 250, as described above.

While the present invention has been primarily described with respect to tissue ablations within the right atrium of the heart, it will be appreciated that the ablation systems disclosed herein may just as easily be applied to ablation of other tissues, such as the tissue surrounding the sinus cavities, or tissue within the bladder or stomach, for example. The tissue ablations may be performed through either open surgery techniques or through minimal invasive techniques.

Although the foregoing invention has been described in some detail for purposes of clarity of understanding, it will be apparent that certain changes and modifications may be practiced within the scope of the appended claims.

What is claimed is:

1. A method of ablating biological tissue with an ablation apparatus including an elongated member having a flexible distal portion supporting an ablation element to emit ablative energy, the method comprising the steps for;

advancing the distal portion into a patient's body toward a target tissue site;

deflecting the elongated member proximal the distal portion in order to deflect the distal portion in response to contact with tissue at the target tissue site;

additionally deflecting the elongated member to move the distal portion in flexible contact with the tissue along an extended path at the target tissue site; and applying ablative energy to the ablation element during the additional deflecting to ablate tissue along the extended path.

2. The method according to claim 1 wherein the deflecting of the elongated member is in one rotational direction and the flexing of the distal portion is in an opposite rotational direction.

3. The method according to claim 2 wherein the one and the opposite rotational directions are substantially within a common plane.

4. The method according to claim 3 in which the ablation element emits ablative energy substantially aligned with the common plane toward tissue contacted by the flexible distal portion.

5. The method according to claim 1 wherein additional deflecting occurs substantially simultaneously with applying ablative energy for forming a substantially continuous extended path of ablated tissue.

* * * * *